United States Patent

Ladduwahetty et al.

[11] Patent Number: 6,054,456
[45] Date of Patent: Apr. 25, 2000

[54] SUBSTITUTED PIPERAZINE DERIVATIVES

[75] Inventors: Tamara Ladduwahetty, London; Angus Murray MacLeod, Bishops Stortford; Michael Rowley, Harlow, all of United Kingdom

[73] Assignee: Merck Sharp & Dohme Ltd., Hoddesdon, United Kingdom

[21] Appl. No.: 09/077,618

[22] PCT Filed: Nov. 21, 1996

[86] PCT No.: PCT/GB96/02870

§ 371 Date: May 26, 1998

§ 102(e) Date: May 26, 1998

[87] PCT Pub. No.: WO97/19943

PCT Pub. Date: Jun. 5, 1997

[30] Foreign Application Priority Data

Nov. 29, 1995 [GB] United Kingdom .................. 9524356

[51] Int. Cl.[7] ...................... A61K 31/496; C07D 403/10
[52] U.S. Cl. ................ 514/253; 544/366; 544/362; 544/367; 544/368; 544/369; 544/370; 544/371; 544/372; 544/373; 544/376
[58] Field of Search .................. 544/366, 373; 514/253

[56] References Cited

U.S. PATENT DOCUMENTS

| | | | |
|---|---|---|---|
| 5,780,475 | 7/1998 | Baker et al. | 514/255 |
| 5,808,064 | 9/1998 | Chen et al. | 544/132 |
| 5,919,783 | 7/1999 | Chambers et al. | 514/253 |
| 5,925,638 | 7/1999 | Chambers et al. | 514/253 |
| 5,977,116 | 11/1999 | Castro Pineiro et al. | 514/255 |
| 5,981,529 | 11/1999 | Baker et al. | 514/253 |

FOREIGN PATENT DOCUMENTS

WO 94/02477   2/1994   WIPO .
WO 95/32196   11/1995   WIPO .
WO 96/16056   5/1996   WIPO .

*Primary Examiner*—Emily Bernhardt
*Attorney, Agent, or Firm*—James L. McGinnis; David L. Rose; Philippe L. Durette

[57] ABSTRACT

The present invention provides a compound of formula I, or a pharmaceutically acceptable salt thereof:

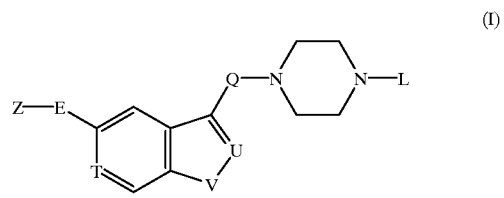

wherein Z, E, Q, T, U, V and L are as defined herein; processes for its preparation and its use in the treatment of conditions for which the administration of an agonist selective for the 5-HT$_{1D\alpha}$ receptor subtype is indicated, such as migraine.

6 Claims, No Drawings

SUBSTITUTED PIPERAZINE DERIVATIVES

The present invention relates to a class of substituted piperazine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309–11; and W. Feniuk and P. P. A. Humphrey, *Drug Development Research*, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D\alpha}$ (or 5-HT$_{1D-1}$) and 5-HT$_{1D\beta}$ (or 5-HT$_{1D-2}$), and their amino acid sequences are disclosed and claimed in WO-A-91/17174.

The 5-HT$_{1D\alpha}$ receptor subtype in humans is believed to reside on sensory terminals in the dura mater. Stimulation of the 5-HT$_{1D\alpha}$ subtype inhibits the release of inflammatory neuropeptides which are thought to contribute to the headache pain of migraine. The human 5-HT$_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.*, 1992, 304, 1415; J. P. Ottervanger et al., *The Lancet*, 1993, 341, 861–2; and D. N. Bateman, *The Lancet*, 1993, 341, 221–4). Since sumatriptan barely discriminates between the human 5-HT$_{1D\alpha}$ and 5-HT$_{1D\beta}$ receptor subtypes (cf. WO-A-91/171174, Table 1), and since it is the blood vessels with which the 5-HT$_{1D\beta}$ subtype is most closely associated, it is believed that the cardiovascular side-effects observed with sumatriptan can be attributed to stimulation of the 5-HT$_{1D\beta}$ receptor subtype. It is accordingly considered (cf. G. W. Rebeck et al., *Proc. Natl. Acad. Sci. USA*, 1994, 91, 3666–9) that compounds which can interact selectively with the 5-HT$_{1D\alpha}$ receptor subtype, whilst having a less pronounced action at the 5-HT$_{1D\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D\alpha}$ receptor subtype. Moreover, the compounds in accordance with this invention have been found to possess at least a 10-fold selective affinity for the 5-HT$_{1D\alpha}$ receptor subtype relative to the 5-HT$_{1D\beta}$ subtype, and then can therefore be expected to manifest fewer side-effects than those associated with non-subtype-selective 5-HT$_{1D}$ receptor agonists.

Several distinct classes of substituted five-membered heteroaromatic compounds are described in published European patent applications 0438230, 0494774 and 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the piperazine derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the alkoxypyridine or alkoxypyrimidine substituent with an aryl- or heteroaryl-substituted fluoro- or difluoromethylcarbonyl or -thiocarbonyl moiety.

WO-A-91/18897 describes a class of tryptamine derivatives substituted by various five-membered rings, which are stated to be specific to a particular type of "5-HT$_1$-like" receptor and thus to be effective agents for the treatment of clinical conditions, particularly migraine, requiring this activity. A further class of tryptamine derivatives with alleged antimigraine activity is disclosed in WO-A-94/02460. However, neither WO-A-91/18897 nor WO-A-94/02460 discloses or suggests the piperazine derivatives provided by the present invention.

Moreover, nowhere in the prior art mentioned above is there any disclosure of a subtype-selective 5-HT$_{1D}$ receptor agonist having a 5-HT$_{1D\alpha}$ receptor binding affinity (IC$_{50}$) below 50 nM and at least a 10-fold selective affinity for the 5-HT$_{1D\alpha}$ receptor subtype relative to the 5-HT$_{1D\beta}$ subtype.

The compounds according to the present invention are subtype-selective 5-HT$_{1D}$ receptor agonists having a human 5-HT$_{1D\alpha}$ receptor binding affinity (IC$_{50}$) below 50 nM, typically below 10 nM and preferably below 1 nM; and at least a 10-fold selective affinity, typically at least a 50-fold selective affinity and preferably at least a 100-fold selective affinity, for the human 5-HT$_{1D\alpha}$ receptor subtype relative to the 5-HT$_{1D\beta}$ subtype. Moreover the compounds in accordance with this invention possess interesting properties in terms of their efficacy and/or bioavailability.

The present invention provides a compound of formula I, or a salt or prodrug thereof:

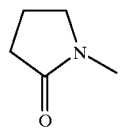

(Za)

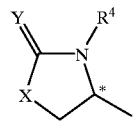

(Zb)

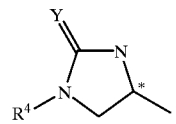

(Zc)

-continued

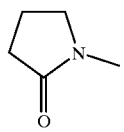
(Zd)

wherein

Z represents hydrogen, halogen, cyano, nitro, trifluoromethyl, —OR$^5$, —OCOR$^5$, —OCONR$^5$R$^6$, —OCH$_2$CN, —OCH$_2$CONR$^5$R$^6$, —SR$^5$, —SOR$^5$, —SO$_2$R$^5$, —SO$_2$NR$^5$R$^6$, —NR$^5$R$^6$, —NR$^5$COR$^6$, —NR$^5$CO$_2$R$^6$, —NR$^5$SO$_2$R$^6$, —COR$^5$, —CO$_2$R$^5$, —CONR$^5$R$^6$, or a group of formula (Za), (Zb), (Zc) or (Zd):

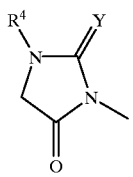
(Za)

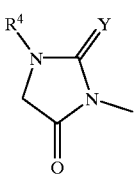
(Zd)

in which the asterisk * denotes a chiral centre; or

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

X represents oxygen, sulphur, —NH— or methylene;

Y represents oxygen or sulphur:

E represents a chemical bond or a straight or branched alkylene chain containing from 1 to 4 carbon atoms;

Q represents a straight or branched alkylene chain containing from 1 to 6 carbon atoms, optionally substituted in any position by one or more substituents selected from fluoro and hydroxy;

T represents nitrogen or CH;

U represents nitrogen or C—R$^2$;

V represents oxygen, sulphur or N—R$^3$;

R$^2$, R$^3$ and R$^4$ independently represent hydrogen or C$_{1-6}$ alkyl; and

R$^5$ and R$^6$ independently represent hydrogen, C$_{1-6}$ alkyl, trifluoromethyl, phenyl, methylphenyl, or an optionally substituted aryl(C$_{1-6}$)alkyl or heteroaryl(C$_{1-6}$)alkyl group; or R$^5$ and R$^6$, when linked through a nitrogen atom, together represent the residue of an optionally substituted azetidine, pyrrolidine, piperidine, morpholine or piperazine ring;

L is selected from:

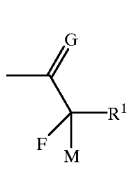
(A)

wherein:
G represents oxygen or sulphur;
M represents halogen or C$_{1-6}$ alkyl;
R$^1$ represents aryl or heteroaryl, either of which groups may be optionally substituted;

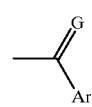
(B)

wherein: Ar is a six-membered aromatic ring optionally containing one or two nitrogen atoms, which ring is unsubstituted or substituted by one or more substituents independently selected from halogen, nitro, cyano, amino. C$_{1-6}$alkyl, C$_{2-6}$alkenyl, C$_{2-6}$alkynyl, CF$_3$, C$_{1-6}$alkoxy, C$_{2-6}$alkenyloxy, C$_{2-6}$alkynyloxy, OR$^7$, C$_{1-6}$alkylthio, C$_{2-6}$alkenylthio, C$_{2-6}$-calkynylthio and SR$^7$; where R$^7$ is phenyl optionally substituted by halogen, nitro, cyano, amino, methoxy or CF$_3$; and G is as defined above; and

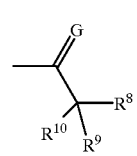
(C)

wherein: R$^8$ is phenyl which is unsubstituted or substituted with one or more substituents independently selected from halogen, cyano, nitro, amino, C$_{1-3}$alkyl, C$_{1-3}$alkoxy and CF$_3$;
R$^9$ and R$^{10}$ are independently selected from hydrogen, C$_{1-6}$alkyl, C$_{2-6}$alkyl, C$_{2-6}$alkenyl, C$_{2-6}$alkynyl and halogen, or R$^9$ and R$^{10}$, together with the carbon atom to which they are attached, form a C$_{3-7}$cycloalkyl group; and
G is as defined above.

The present invention also provides a compound of formula (I'), or a salt of prodrug thereof:

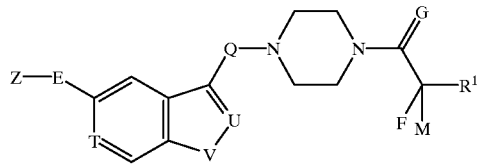
(I')

in which Z, E, T, V, U, Q, G, M and R$^1$ are as defined above.

Ar is suitably a phenyl ring. Ar may be unsubstituted. Ar may be substituted with one, two or three substituents independently selected from halogen, cyano, nitro, $C_{1-6}$alkoxy, $C_{2-6}$alkenyloxy, $C_{2-6}$alknyloxy and $OR^7$; preferably from $C_{1-6}$calkoxy and $OR^7$. most preferably from $OR^7$. Ar is preferably mono-substituted. $R^7$ is suitably phenyl which is unsubstituted or substituted by halogen. $R^7$ is preferably unsubstituted.

Where Z in the compounds of formula I above represents a five-membered heteroaromatic ring, this ring may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include $C_{1-6}$ alkyl, $C_{2-6}$ alkenyl, $C_{2-6}$ alkynyl, $C_{3-7}$ cycloalkyl, aryl, aryl($C_{1-6}$) alkyl, $C_{3-7}$ heterocycloalkyl, heteroaryl, heteroaryl($C_{1-6}$) alkyl, $C_{1-6}$ alkoxy, $C_{1-6}$ alkylthio, amino, $C_{1-6}$ alkylamino, di($C_{1-6}$)alkylamino, halogen, cyano and trifluoromethyl.

The group $R^1$ may be optionally substituted by one or more substituents, as also may the groups $R^5$ or $R^6$ where these represent aryl($C_{1-6}$)alkyl or heteroaryl($C_{1-6}$)alkyl. Where $R^5$ or $R^6$ represents aryl($C_{1-6}$)alkyl or heteroaryl($C_{1-6}$)alkyl, any optional substitution will suitably be on the aryl or heteroaryl moiety thereof, although substitution on the alkyl moiety thereof is an alternative possibility. Examples of optional substituents thereon include halogen, cyano, trifluoromethyl, triazolyl, tetrazolyl, $C_{1-6}$ alkyl-tetrazolyl, hydroxy, $C_{1-6}$ alkoxy, $C_{1-6}$ alkylthio, $C_{2-6}$ alkoxycarbonyl, $C_{2-6}$ alkylcarbonyl, $C_{1-6}$ alkylsulphonyl, arylsulphonyl, amino, $C_{1-6}$ alkylamino, di($C_{1-6}$)alkylamino, di($C_{1-6}$)alkylaminomethyl, $C_{2-6}$ alkylcarbonylamino, arylcarbonylamino, $C_{2-6}$ alkoxycarbonylamino, N-($C_{1-6}$)alkyl-N-($C_{2-6}$)alkoxycarbonylamino, $C_{1-6}$ alkylsulphonylamino, arylsulphonylamino, $C_{1-6}$ alkylsulphonylaminomethyl, aminocarbonylamino, $C_{1-6}$ alkylaminocarbonylamino, di($C_{1-6}$) alkylaminocarbonylamino, mono- or diarylaminocarbonylamino, pyrrolidinylcarbonylamino, piperidinylcarbonylamino, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$) alkylaminosulphonyl, aminosulphonylmethyl, $C_{1-6}$ alkylaminosulphonylmethyl and di($C_{1-6}$) alkylaminosulphonylmethyl.

When $R^5$ and $R^6$, when linked through a nitrogen atom, together represent the residue of an azetidine, pyrrolidine, piperidine, morpholine or piperazine ring, this ring may he unsubstituted or substituted by one or more substituents. Examples of suitable substituents include $C_{1-6}$ alkyl, aryl ($C_{1-6}$)alkyl, $C_{1-6}$ alkoxy, $C_{2-6}$ alkoxycarbonyl and $C_{1-6}$ alkylaminocarbonyl. Typical substituents include methyl, benzyl, methoxy, methoxycarbonyl, ethoxycarbonyl and methylaminocarbonyl. In particular, where $R^5$ and $R^6$ together represent the residue of a piperazine ring, this ring is preferably substituted on the distal nitrogen atom by a $C_{2-6}$ alkoxycarbonyl moiety such as methoxycarbonyl or ethoxycarbonyl.

$R^8$ may be unsubstituted. $R^8$ may be substituted with halogen, cyano, nitro or $C_{1-3}$ alkyl, preferably with halogen, most preferably with fluoro. $R^8$ is preferably unsubstituted or mono-substituted in the 2-, 3- or 4-position.

$R^9$ and $R^{10}$ are suitably independently selected from hydrogen, halogen and $C_{1-3}$ alkyl or form, together with the carbon atom to which they are attached, a $C_{5-6}$ cycloalkyl group. $R^9$ and $R^{10}$ are preferably independently selected from hydrogen, fluorine and methyl or form, together with the carbon atom to which they are attached, a cyclopentyl group.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and t-butyl. Derived expressions such as "$C_{1-6}$ alkoxy", "$C_{1-6}$ alkylthio" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl, allyl, dimethylallyl and butenyl groups.

The expression "$C_{2-6}$ alkynyl" as used herein refers to straight-chained and branched alkynyl groups containing from 2 to 6 carbon atoms. Typical examples include ethynyl and propargyl groups.

Typical $C_{3-7}$ cycloalkyl groups include cyclopropyl, cyclobutyl, cyclopentyl and cyclohexyl.

Typical aryl groups include phenyl and naphthyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridylmethyl, pyridylethyl, pyrimidinylmethyl, pyrazinylmethyl, quinolylmethyl and isoquinolylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, funiaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. For example, the compounds of formula I above wherein Z represents a group of formula (Zb) or (Zc) have a chiral centre denoted by the asterisk *, which may accordingly be in the (R) or (S) configuration. It is to be understood that all such isomers and mixtures thereof in any proportion are encompassed within the scope of the present invention.

Where E and Q, which may be the same or different, represent straight or branched alkylene chains, these may be, for example, methylene, ethylene, 1-methylethylene, propylene, 2-methylpropylene or butylene. In addition, the alkylene chain Q may be substituted in any position by one or more substituents selected from fluoro and hydroxy giving rise, for example, to a 2-hydroxypropylene, 2-hydroxymethylpropylene, 2-fluoropropylene or 2-fluoromethyl-propylene chain Q. Moreover, E may represent a chemical bond such that the moiety Z is attached directly to the central fused bicyclic heteroaromatic ring system containing the variables T, U and V.

Suitably, E represents a chemical bond or a methylene linkage.

Representative alkylene chains for Q include propylene, butylene, 2-hydroxypropylene, 2-hydroxymethyl-propylene, 2-fluoropropylene and 2-fluoromethyl-propylene, especially propylene.

The compound of formula I in accordance with the present invention is suitably an indole, benzofuran or benzthiophene derivative of formula IA, an indazole derivative of formula IB, or a pyrrolo[2,3-c]-pyridine derivative of formula IC:

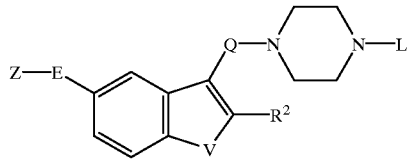

(IA)

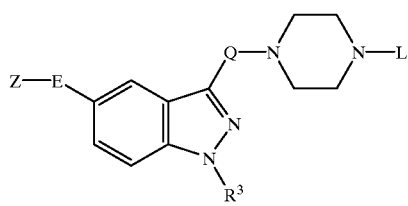

(IB)

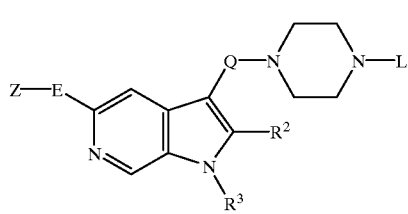

(IC)

wherein Z, E, Q, V, $R^2$, $R^3$ and L are as defined above.

A subclass of each of these derivatives of formulae I'A, I'B and I'C is also disclosed:

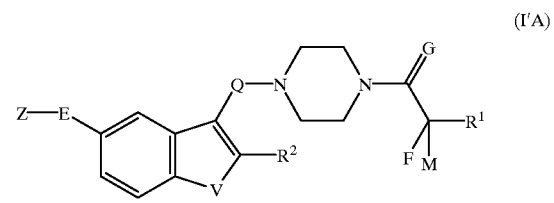

(I'A)

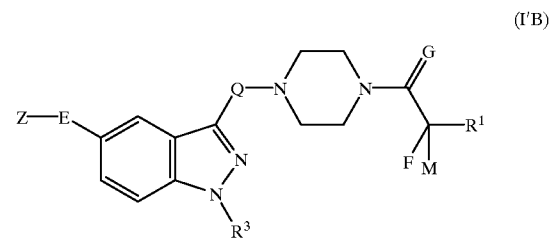

(I'B)

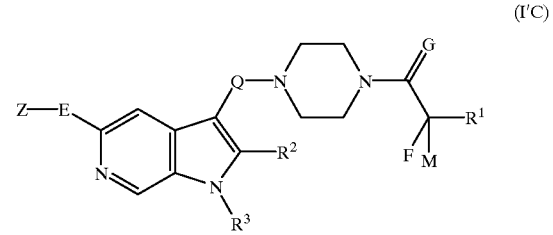

(I'C)

wherein Z, E, Q, V, G, M, $R^1$, $R^2$ and $R^3$ are as defined above. Preferably, the compounds according to the invention are indole or pyrrolo[2,3-c]pyridine derivatives of formulae ID, I'D or I"D:

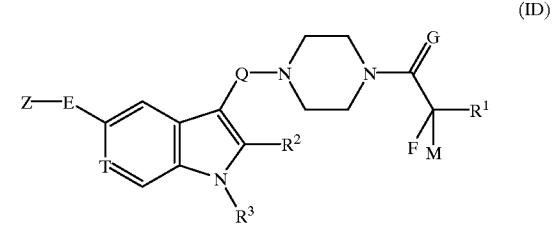

(ID)

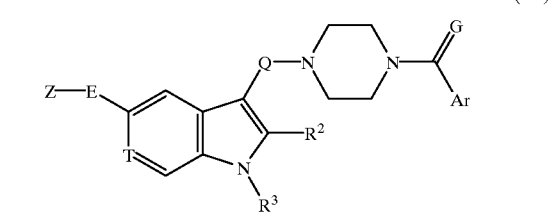

(I'D)

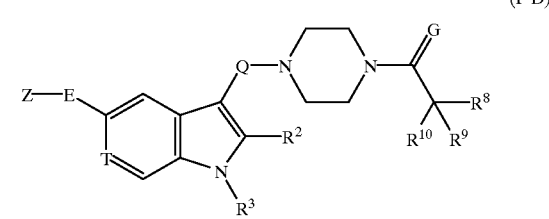

(I"D)

wherein Z, E, Q, T, G, M, $R^1$, $R^2$, $R^3$, $R^8$, $R^9$, $R^{10}$ and Ar are as defined above, in particular wherein $R^2$ and $R^3$ are both hydrogen.

Suitably, Ar represents phenyl optionally substituted by phenoxy.

Suitably, G represents oxygen.

Suitably, M represents fluoro or methyl, especially fluoro.

Suitably, $R^1$ represents phenyl, optionally substituted by one or more substituents selected typically from halogen, cyano, trifluoromethyl, triazolyl, tetrazolyl, $C_{1-6}$ alkyl-tetrazolyl, $C_{1-6}$ alkoxy, amino, di($C_{1-6}$)alkylamino, di($C_{1-6}$) alkylaminomethyl, $C_{2-6}$ alkylcarbonylamino, $C_{2-6}$ alkoxycarbonylamino, N-($C_{1-6}$)alkyl-N-($C_{2-6}$) alkoxycarbonylamino, $C_{1-6}$ alkylsulphonylamino, aminocarbonylamino, aminocarbonyl, $C_{1-6}$ alkylaminocarbonyl, di($C_{1-6}$)alkylaminocarbonyl, aminosulphonyl and $C_{1-6}$ alkylaminosulphonylmethyl.

Particular values of $R^1$ include phenyl, fluorophenyl and difluorophenyl.

Suitably, $R^2$ and $R^3$ independently represent hydrogen or methyl, especially hydrogen.

Suitably, $R^4$ represents hydrogen or methyl, especially hydrogen.

Suitably, $R^5$ and $R^6$ are independently, selected from hydrogen, methyl, ethyl, n-propyl, isopropyl, n-butyl, t-butyl, trifluoromethyl, phenyl, methylphenyl (especially 4-methylphenyl), benzyl and phenethyl.

Suitably, $R^8$ represents phenyl.

Suitably, $R^9$ and $R^{10}$ are independently selected from hydrogen, halogen, especially fluorine, and methyl or $R^9$ and $R^{10}$, together with the carbon atom to which they are attached, form a cyclopentyl group.

Suitably, the substituent Z represents hydrogen, fluoro, cyano, hydroxy, methoxy, ethoxy, benzyloxy, methylamino-carbonyloxy, cyanomethoxy, aminocarbonyl-methoxy, methylsulphonyl, aminosulphonyl, N-methylamino-sulphonyl, N,N-dimethylamino-sulphonyl, amino, formylamino, acetylamino, trifluoromethyl-carbonylamino, benzyloxycarbonylamino, methyl-sulphonylamino, ethyl-sulphonylamino, methylphenyl-sulphonylamino, N-methyl-(N-methylsulphonyl)-amino, N-methyl-(N-ethylsulphonyl)-amino, N-methyl-(N-trifluoromethylsulphonyl)-amino, N-ethyl-(N-methylsulphonyl)-amino, N-benzyl-(N-methylsulphonyl)-amino, N-benzyl-(N-ethylsulphonyl)-amino, acetyl, methoxycarbonyl, ethoxycarbonyl, aminocarbonyl, methylaminocarbonyl, ethylaminocarbonyl, propylaminocarbonyl, butylaminocarbonyl, benzylaminocarbonyl or phenethyl-aminocarbonyl; or a group of formula (Za), (Zb), (Zc) or (Zd) as defined above; or an optionally substituted five-membered heteroaromatic ring as specified above.

In a particular embodiment, Z represents —$SO_2NR^5R^6$ in which $R^5$ and $R^6$ are as defined above. In a subset of this embodiment, $R^5$ and $R^6$ independently represent hydrogen or $C_{1-6}$ alkyl, especially hydrogen or methyl. Particular values of Z in this context include aminosulphonyl, N-methylamino-sulphonyl and N,N-dimethylamino-sulphonyl, especially N-methylamino-sulphonyl.

In another embodiment, Z represents a group of formula (Zb) in which $R^4$ is hydrogen or methyl. In a subset of this embodiment, X and Y both represent oxygen. In a particular aspect of this subset, the chiral centre denoted by the asterisk * is in the (S) configuration.

When the group Z represents an optionally substituted five-membered heteroaromatic ring, this is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, 1,2,4-oxadiazole, 1,2,4-thiadiazole or 1,2,4-triazole ring, in particular a 1,2,4-triazol-1-yl or 1,2,4-triazol-4-yl moiety.

Suitably, the five-membered heteroaromatic ring Z is unsubstituted. Examples of optional substituents which may typically be attached to the moiety Z include methyl, ethyl, benzyl and amino.

A particular sub-class of compounds according to the invention is represented by the compounds of formula IIA, and salts and prodrugs thereof:

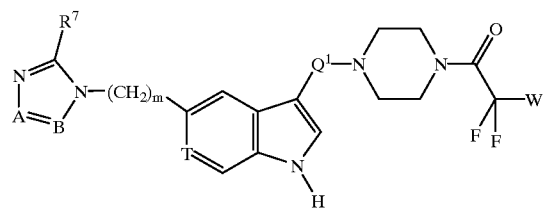

(IIA)

wherein m is zero, 1, 2 or 3, preferably zero or 1;

$Q^1$ represents a straight or branched alkylene chain containing from 2 to 5 carbon atoms, optionally substituted in any position by one or more substituents selected from fluoro and hydroxy;

T represents nitrogen or CH;

A represents nitrogen or CH;

B represents nitrogen or C—$R^{11}$;

$R^7$ and $R^{11}$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl;

W represents a group of formula (Wa), (Wb) or (Wc):

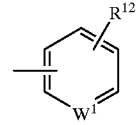

(Wa)

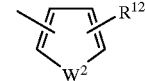

(Wb)

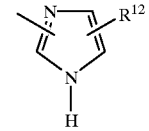

(Wc)

in which $W^1$ represents CH or nitrogen;

$W^2$ represents oxygen, sulphur, NH or N-methyl; and $R^{12}$ represents hydrogen, halogen, cyano, trifluoromethyl, triazolyl, tetrazolyl, $C_{1-6}$ alkyl-tetrazolyl, $C_{1-6}$ alkoxy, $C_{2-6}$ alkylcarbonyl, amino, $C_{1-6}$ alkylamino, di($C_{1-6}$)alkylamino, di($C_{1-6}$) alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl.

Suitably, $Q^1$ represents a straight or branched 3 or 4 carbon alkylene chain, optionally substituted in any position by one or more substituents selected from fluoro and hydroxy. Particular alkylene chains for $Q^1$ include propylene, butylene, 2-hydroxypropylene, 2-(hydroxymethyl)-propylene, 2-fluoropropylene and 2-(fluoromethyl)-propylene, especially propylene.

Particular values of $R^7$ and $R^{11}$ include hydrogen, methyl, ethyl, benzyl and amino, especially hydrogen.

Particular values of $R^{12}$ include hydrogen, fluoro, cyano, triazolyl, tetrazolyl, methyl-tetrazolyl, methoxy, amino, dimethylaminomethyl, acetylamino, aminocarbonylamino, methylaminocarbonyl and aminosulphonyl, especially hydrogen or fluoro.

Another sub-class of compounds according to the invention is represented by the compounds of formula IIB, and salts and prodrugs thereof:

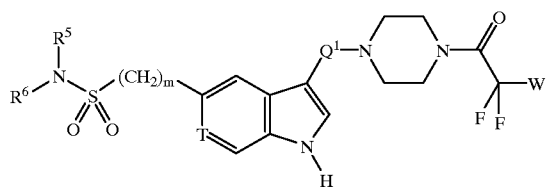

(IIB)

wherein m, $Q^1$, T and W are as defined with reference to formula IIA above; and $R^5$ and $R^6$ are as defined with reference to formula I above.

Particular values of $R^5$ and $R^6$ in relation to formula IIB above include hydrogen and $C_{1-6}$ alkyl, especially hydrogen or methyl. Suitably, one of $R^5$ and $R^6$ represents hydrogen and the other represents hydrogen or methyl.

A further sub-class of compounds according to the invention is represented by the compounds of formula IIC, and salts and prodrugs thereof:

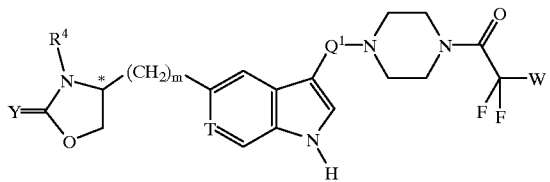

(IIC)

wherein the asterisk * denotes a chiral centre;

m, $Q^1$, T and W are as defined with reference to formula IIA above: and $R^4$ and Y are as defined with reference to formula I above.

Particular values of $R^4$ in relation to formula IIC include hydrogen and methyl.

Preferably, Y in formula IIC is oxygen.

Preferably, the chiral centre denoted by the asterisk * in formula IIC is in the (S) configuration.

In a particular embodiment of the compounds of formulae IIA, IIB and IIC above, W represents a group of formula (Wa) in which $W^1$ is CH.

Specific compounds within the scope of the present invention include:
4-(2,2-difluoro-1-oxo-2-phenylethyl)-1-[3-(5-(1,2,4-triazol-4-yl)-1H-indol-3-yl)propyl]piperazine;
1-[3-(5-(1,2,4-triazol-4-yl)-1H-indol-3-yl)propyl]-4-(1-phenyl-1-cyclopentylmethanoyl)piperazine;
1-[3-(5-(1,2,4-triazol-4-yl)-1H-indol-3-yl)propyl]-4-(2-phenoxybenzoyl)piperazine;
1-[3-(5-(1,2,4-triazol-4-yl)-1H-indol-3-yl)propyl]-4-[(R,S)-2-(2-fluorophenyl)propanoyl]piperazine;
1-[3-(5-(1,2,4-triazol-4-yl)-1H-indol-3-yl)propyl]-4-[(R,S)-2-(3-fluorophenyl)propanoyl]piperazine;
1-[3-(5-(1,2,4-triazol-4-yl)-1H-indol-3-yl)propyl]-4-[(R,S)-2-(4-fluorophenyl)propanoyl]piperazine;
1-[3-(5-(1,2,4-triazol-4-yl)-1H-indol-3-yl)propyl]-4-(4-fluorophenylethanoyl)piperazine;
and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The present invention also provides a compound according to the present invention, or a pharmaceutically acceptable salt or prodrug thereof, for use in a method of treatment of the human or animal body. Suitably the compound is used in a method for which the administration of an agonist selective for the 5-HT$_{1D\alpha}$ receptor subtype is indicated, such as in the treatment of migraine.

There is also provided the use of a compound according to the present invention, or a pharmaceutically acceptable salt or prodrug thereof, in the manufacture of a medicament for the treatment or prophylaxis of a condition for which the administration of an agonist selective for the 5-HT$_{1D\alpha}$ subtype is indicated, such as migraine.

There is also disclosed a method of treatment of a subject suffering from or prone to a condition for which the administration of an agonist selective for the 5-HT$_{1D\alpha}$ receptor subtype is indicated. such as migraine. which comprises administering to that subject a therapeutically or prophylactically effective amount of a compound according to the present invention or a pharmaceutically acceptable salt or prodrug thereof.

The compounds according to the invention wherein G represents oxygen may be prepared by a process which comprises reacting a compound of formula III with a compound of formula IV:

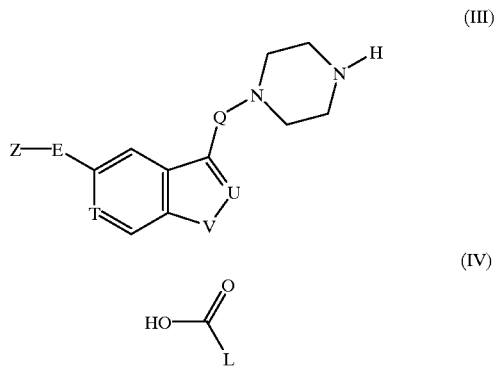

wherein Z, E, Q, T, U, V and L are as defined above.

The reaction is conveniently carried out in a solvent such as dichloromethane or DMF, typically in the presence of a base such as triethylamine, optionally using a catalyst such as hydrobenzotriazole and a coupling agent such as 1-(3-dimethylaminopropyl)-3-ethylcarbodiimide methiodide.

The compounds of formula III above wherein T represents CH, U represents C—R$^2$ and V represents N—R$^3$ may be prepared by a process which comprises reacting a compound of formula V:

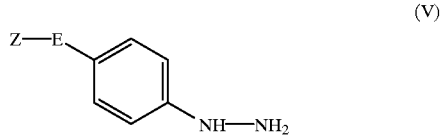

wherein Z and E are as defined above: with a compound of formula VI, or a carbonyl-protected form thereof:

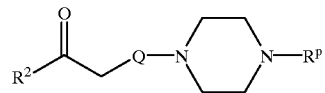

wherein R$^2$ and Q are as defined above, and R$^p$ represents an amino-protecting group; followed, where required, by N-alkylation by standard methods to introduce the moiety R$^3$; with subsequent removal of the amino-protecting group R$^p$.

The reaction between compounds V and VI, which is an example of the well-known Fischer indole synthesis, is suitably carried out by heating the reagents together under mildly acidic conditions, e.g. 4% sulphuric acid at reflux.

Suitable carbonyl-protected forms of the compounds of formula VI include the dimethyl acetal or ketal derivatives.

The protecting group R$^p$ in the compounds of formula VI is suitably a carbamoyl moiety such as t-butoxycarbonyl (BOC), which can conveniently be removed as necessary by treatment under mildly acidic conditions. Indeed, the acidic conditions of the Fischer indole synthesis reaction will generally suffice to remove the BOC group.

The Fischer reaction between compounds V and VI may be carried out in a single step, or may proceed via an initial non-cyclising step at a lower temperature to give an intermediate of formula VII:

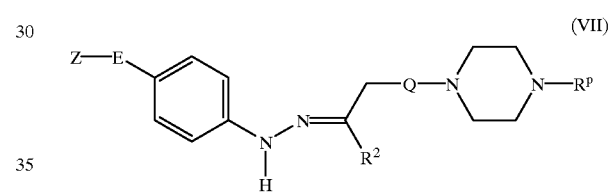

wherein Z, E, Q, R$^2$ and R$^p$ are as defined above; followed by cyclisation using a suitable reagent, e.g. a polyphosphate ester.

The intermediates of formula VI, or carbonyl-protected forms thereof, may be prepared by reacting a compound of formula VIII, or a carbonyl-protected form thereof, with a compound of formula IX:

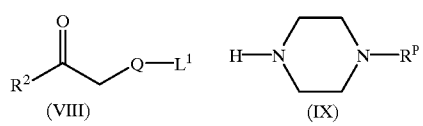

wherein Q, R$^2$ and R$^p$ are as defined above, and L$^1$ represents a suitable leaving group.

The leaving group L$^1$ is suitably a halogen atom, e.g. chlorine or bromine.

Where L$^1$ represents a halogen atom, the reaction between compounds VIII and IX is conveniently effected by stirring the reactants under basic conditions in a suitable solvent, for example potassium carbonate in N,N-dimethylformamide, or triethylamine in tetrahydrofuran or acetonitrile.

The compounds according to the invention wherein T represents CH, U represents C—R$^2$ and V represents N—R$^3$—i.e. the indole derivatives of formula ID as defined above wherein T represents CH—may alternatively be prepared by a process which comprises reacting a compound of formula V as defined above with a compound of formula X, or a carbonyl-protected form thereof:

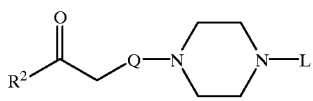

(X)

wherein Q, L and $R^2$ are as defined above; under conditions analogous to those described above for the reaction between compounds V and VI: followed, where required, by N-alkylation by standard methods to introduce the moiety $R^3$.

As for the compounds of formula VI, suitable carbonyl-protected forms of the compounds of formula X include the dimethyl acetal or ketal derivatives.

As with that between compounds V and VI, the Fischer reaction between compounds V and X may be carried out in a single step, or may proceed via an initial non-cyclising step at a lower temperature to give an intermediate of formula XI:

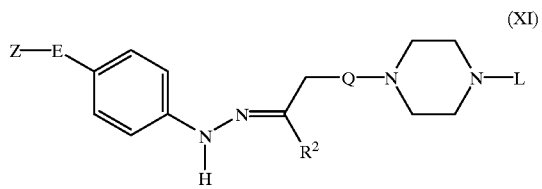

(XI)

wherein Z, E, Q, L and $R^2$ are as defined above; followed by cyclisation using a suitable reagent, e.g. a polyphosphate ester.

The intermediates of formula X, or carbonyl-protected forms thereof, may be prepared by reacting a compound of formula VIII as defined above, or a carbonyl-protected form thereof, with a compound of formula XII:

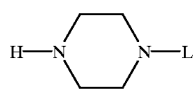

(XII)

wherein L is as defined above; under conditions analogous to those described above for the reaction between compounds VIII and IX.

In an alternative procedure, the compounds of formula III above may be prepared by a process which comprises reacting a compound of formula IX as defined above with a compound of formula XIII:

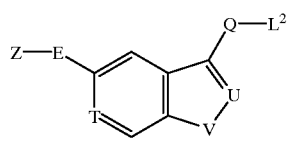

(XIII)

wherein Z, E, Q, T, U and V are as defined above, and $L^2$ represents a suitable leaving group; followed by removal of the amino-protecting group $R^p$.

Similarly, the compounds of formula I as defined above may be prepared by a process which comprises reacting a compound of formula XII as defined above with a compound of formula XIII as defined above.

The leaving group $L^2$ is suitably an alkylsulphonyloxy or arylsulphonyloxy group, e.g. methanesulphonyloxy (mesyloxy) or p-toluenesulphonyloxy (tosyloxy).

Where $L^2$ represents an alkylsulphonyloxy or arylsulphonyloxy group, the reaction between compound XIII and compound IX or XII is conveniently carried out in a suitable solvent such as 1,2-dimethoxyethane or isopropyl alcohol, typically in the presence of a base such as sodium carbonate or potassium carbonate. optionally with the addition of sodium iodide.

In one representative approach, the compounds of formula XIII wherein T and U both represent CH, V represents NH and $L^2$ represents a mesyloxy or tosyloxy group may be prepared by the sequence of steps illustrated in the following reaction scheme (cf. Larock and Yum, J. Am. Chem. Soc., 1991, 113, 6689):

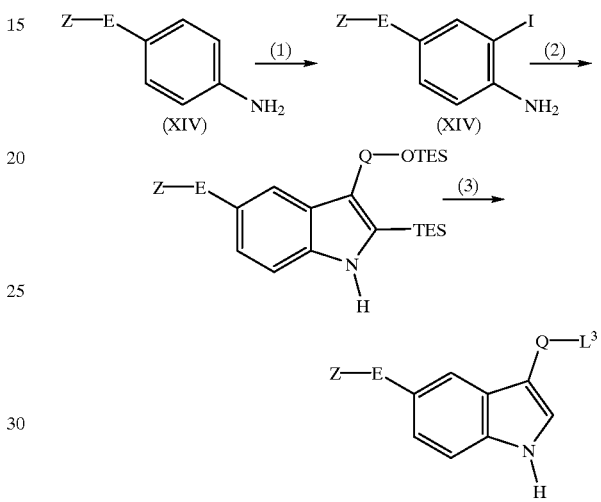

wherein Z, E and Q are as defined above, $L^3$ represents mesyloxy or tosyloxy, and TES is an abbreviation for triethylsilyl.

In Step 1 of the reaction scheme, the aniline derivative XIV is treated with iodine monochloride, typically in methanol or acetonitrile, in order to introduce an iodine atom ortho to the amine moiety. Step 2 involves a palladium-mediated coupling reaction with the protected acetylene derivative TES—C≡C-Q—OTES, typically using palladium acetate and triphenylphosphine in the presence of lithium chloride and sodium carbonate, suitably in N,N-dimethylformamide at an elevated temperature. This is followed in Step 3 by removal of the TES moiety, typically by treatment with hydrochloric acid; followed in turn by mesylation or tosylation, suitably by using mesyl chloride or tosyl chloride respectively in the presence of a base such as triethylamine or pyridine, typically in dichloromethane/acetonitrile.

In another representative approach, the compounds of formula XIII wherein T and U both represent CH, V represents NH, Q represents a propylene chain and $L^2$ represents a mesyloxy or tosyloxy group may be prepared by reacting 3,4-dihydro-2H-pyran with a compound of formula V as defined above or a salt thereof, under a variant of the Fischer reaction conditions as described above for the reaction between compounds V and VI; followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by stirring the pyran derivative with an acid addition salt of the hydrazine derivative V, typically the hydrochloride salt, in an inert solvent such as aqueous ethanol. The resulting hydrazide derivative can then be cyclised by treatment with a Lewis acid such as zinc chloride, in a solvent such as 1,2-dimethoxyethane, suitably at the reflux temperature of the solvent.

In a further procedure, the compounds of formula III above wherein T represents CH, U represents nitrogen and V represents N—R³ may be prepared by a process which comprises cyclising a compound of formula XV:

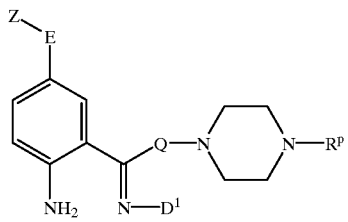

(XV)

wherein Z, E, Q and R^P are as defined above, and D¹ represents a readily displaceable group; followed, where required, by N-alkylation by standard methods to introduce the moiety R³; with subsequent removal of the amino-protecting group R^P.

Similarly, the compounds of formula I wherein T represents CH, U represents nitrogen and V represents N—R³— i.e. the indazole derivatives of formula IB as defined above—may be prepared by a process which comprises cyclising a compound of formula XVI:

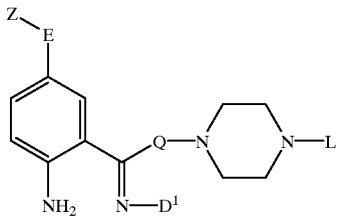

(XVI)

in which Z, E, Q, L and D¹ are as defined above; followed, where required, by N-alkylation by standard methods to introduce the moiety R³.

The cyclisation of compounds XV and XVI is conveniently achieved in a suitable organic solvent at an elevated temperature, for example in a mixture of m-xylene and 2,6-lutidine at a temperature in the region of 140° C.

The readily displaceable group D¹ in the compounds of formula XV and XVI suitably represents a $C_{1-4}$ alkanoyloxy group, preferably acetoxy. Where D¹ represents acetoxy, the desired compound of formula XV or XVI may be conveniently prepared by treating a carbonyl compound of formula XVII:

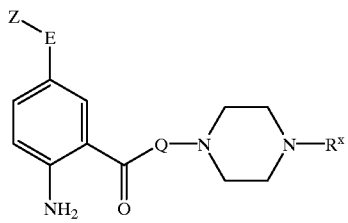

(XVII)

wherein Z, E and Q are as defined above, and R^x represents L where L is as defined above, or R^x represents an amino-protecting group as defined for R^P; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XVII may conveniently be prepared by ozonolysis of the corresponding indole derivative of formula XVIII:

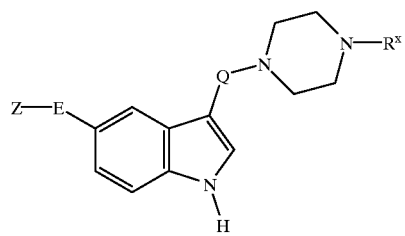

(XVIII)

wherein Z, E, Q and R^x are as defined above; followed by a reductive work-up, advantageously using dimethylsulphide.

The indole derivatives of formula XVIII may be prepared by methods analogous to those described in the accompanying Examples, or by procedures well known from the art.

In a still further procedure, the compounds of formula III above wherein T represents CH, U represents C—R² and V represents oxygen or sulphur may be prepared by a process which comprises cyclising a compound of formula XIX:

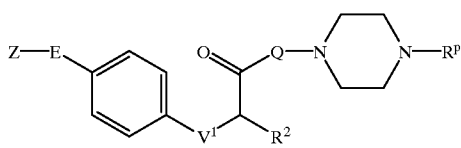

(XIX)

wherein Z, E, Q, R² and R^P are as defined above, and V¹ represents oxygen or sulphur; followed by removal of the amino-protecting group R^P.

Similarly, the compounds of formula I wherein T represents CH, U represents C—R² and V represents oxygen or sulphur—i.e. the benzofuran or benzthiophene derivatives of formula IA above—may be prepared by a process which comprises cyclising a compound of formula XX:

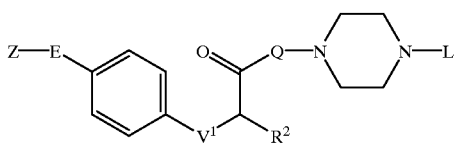

(XX)

wherein Z, E, Q, L, R² and V¹ are as defined above.

The cyclisation of compounds XIX and XX is conveniently effected by using polyphosphoric acid or a polyphosphate ester, advantageously at an elevated temperature.

The compounds of formula XIX and XX may be prepared by reacting a compound of formula XXI with a compound of formula XXII:

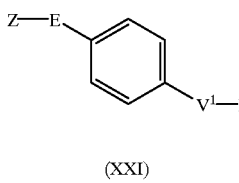
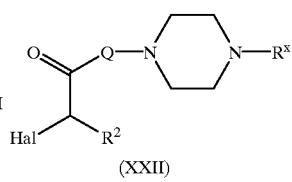

wherein Z, E, Q, $R^2$, $V^1$ and $R^x$ are as defined above, and Hal represents a halogen atom.

The reaction is conveniently effected in the presence of a base such as sodium hydroxide.

The hydroxy and mercapto derivatives of formula XXI may be prepared by a variety of methods which will be readily apparent to those skilled in the art. One such method is described in EP-A-0497512.

The hydrazine derivatives of formula V above may be prepared by methods analogous to those described in EP-A-0438230, EP-A-0497512, EP-A-0548813 and WO-A-91/18897, as also may the aniline derivatives of formula XIV.

Where they are not commercially available, the starting materials of formula IV, VIII, IX, XII and XXII may be prepared by methods analogous to those described in the accompanying Examples, or by standard procedures well known from the art.

In the context of processes for making compounds of the present invention there are also disclosed compounds of formulae IV, X, XI, XII, XVI, XVII and XX in which L is (C=G)—CFM—$R^1$ wherein G, M and $R^1$ are as defined above.

It will be understood that any compound of formula I initially obtained from any of the above processes may, where appropriate, subsequently be elaborated into a further compound of formula I by techniques known from the art. For example, a compound of formula I initially obtained wherein G represents oxygen may be converted into the corresponding compound of formula I wherein G represents sulphur by treatment with Lawesson's reagent (2,4-bis(4-methoxyphenyl)-1,3-dithia-2,4-diphosphetane-2,4-disulphide) under standard conditions. Furthermore, a compound of formula I initially obtained wherein the $R^1$ moiety is substituted by nitro or cyano may be converted by catalytic hydrogenation to the corresponding amino- or aminomethyl-substituted compound respectively. Additionally, a compound of formula I wherein the $R^1$ moiety is substituted by hydroxy, possibly obtained by lithium aluminium hydride reduction of a precursor alkoxycarbonyl derivative, may be mesylated under standard conditions, and the mesyl group subsequently displaced by an amino moiety by treatment with the desired amine in a sealed tube at an elevated temperature. The amine derivative resulting from any of these procedures may then, for example, be N-acylated using the appropriate acyl halide, e.g. acetyl chloride; or aminocarbonylated, using potassium isocyanate, to the corresponding urea derivative; or converted to a 1,2,4-triazol-4-yl derivative using N,N-dimethylformamide azine; or reductively alkylated by treatment with the appropriate aldehyde or ketone in the presence of sodium cyanoborohydride. If desired, the amine derivative may also be carbamoylated by treatment with the requisite alkyl chloroformate. A compound of formula I initially obtained wherein the $R^1$ moiety is substituted by cyano may be converted, by treatment with sodium azide, to the corresponding tetrazole derivative, which in turn may be alkylated on the tetrazole ring by treatment with an alkyl halide under standard conditions. By way of additional illustration, a compound of formula I initially obtained wherein the $R^1$ moiety is substituted by an alkoxycarbonyl moiety may be saponified, by treatment with an alkali metal hydroxide, to the corresponding carboxy-substituted compound, which in turn may be converted to an amide derivative by treatment with the appropriate amine, advantageously in the presence of 1-(3-dimethylaminopropyl)-3-ethylcarbodiumide hydrochloride and 1-hydroxybenzotriazole. Moreover, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in N,N-dimethylformamide.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in *Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the 5-$HT_{1D\alpha}$ receptor subtype, inhibit forskolin-stimulated adenylyl cyclase activity, and stimulate [$^{35}$S]-GTPγS binding to membranes from clonal cell lines expressing human cloned receptors.

5-$HT_{1D\alpha}$/5-$HT_{1D\beta}$ Radioligand Binding

Chinese hamster ovary (CHO) clonal cell lines expressing the human 5-$HT_{1D\alpha}$ and 5-$HT_{1D\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, $CaCl_2$ 4; ascorbate 0.1%: pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]- 5-HT for displacement studies. The final assay volume was 1 ml. 5-HT (10 μM) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which $IC_{50}$ (the molar concentration of compound necessary to inhibit binding by 50%) values could be calculated for each test compound. The $IC_{50}$ values for binding to the 5-$HT_{1D\alpha}$ receptor subtype obtained for the compounds of the accompanying Examples were below 50 nM in each case. Furthermore, the compounds of the accompanying Examples were all found to possess a selective affinity for the 5-$HT_{1D\alpha}$ receptor subtype of at least 10-fold relative to the 5-$HT_{1D\beta}$ subtype.

5-$HT_{1D\alpha}$/5-$HT_{1D\beta}$ Adenylyl Cyclase Assay

Studies were performed essentially as described in *J. Pharmacol. Exp. Ther.*, 1986, 238, 248. CHO clonal cell lines expressing the human cloned 5-$HT_{1D\alpha}$ and 5-$HT_{1D\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of $\alpha$-[$^{33}$P]-ATP to [$^{33}$P]-cyclic AMP. A 10 µl aliquot of the membrane suspension was incubated, for 10–15 min, in a final volume of 50 µl, at 30° C., with or without forskolin (10 µM), in the presence or absence of test compound. The incubation buffer consisted of 50 mM Tris HCl (pH 7.6 at room temperature), 100 mM NaCl, 30 µM GTP, 50 µM cyclic AMP, 1 mM dithiothreitol, 1 mM ATP, 5 mM $MgCl_2$, 1 mM EGTA, 1 mM 3-isobutyl-1-methylxanthine, 3.5 mM creatinine phosphate, 0.2 mg/ml creatine phosphokinase, 0.5–1 µCi $\alpha$-[$^{33}$P]-ATP and 1 nCi [$^{3}$H]-cyclic AMP. The incubation was initiated by the addition of membrane, following a 5 min preincubation at 30° C., and was terminated by the addition of 100 µl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochein.*, 1974, 58, 541). Functional parameters were determined using a least squares curve fitting programme ALLFIT (*Am. J. Physiol.*, 1978, 235, E97) from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D\alpha}$ receptor subtype relative to the 5-$HT_{1D\beta}$ subtype.

5-$HT_{1D\alpha}$/5-$HT_{1D\beta}$ GTPγS Binding

Studies were performed essentially as described in *Br. J. Pharmacol.*, 1993, 109, 1120. CHO clonal cell lines expressing the human cloned 5-$HT_{1D\alpha}$ and 5-$HT_{1D\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA. pH 7.4 at room temperature and recentrifuged at 40,000 g, 4° C. for 15–25 minutes. The membranes were then resuspended in assay buffer (composition in mM: HEPES 20, NaCl 100, $MgCl_2$ 10, pargyline 0.01; ascorbate 0.1%; pH 7.4 at room temperature) at a concentration of 40 µg protein/ml for the 5-$HT_{1D\alpha}$ receptor transfected cells and 40–50 µg protein/ml for the 5-$HT_{1D\beta}$ receptor transfected cells. The membrane suspension was then incubated, in a volume of 1 ml, with GDP (100 µM for 5-$HT_{1D\alpha}$ receptor transfected cells, 30 µM for the 5-$HT_{1D\beta}$ receptor transfected cells) and test compound at 30° C. for 20 min and then transferred to ice for a further 15 min. [$^{35}$S]-GTPγS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D\alpha}$ receptor subtype relative to the 5-$HT_{1D\beta}$ subtype.

PREPARATION 1

4'-(1,2,4-Triazol-4-yl)phenylhydrazine

Prepared as described in WO 94/03446.

PREPARATION 2

1-(3-[5-(1,2,4-Triazol-4-yl)-1H-indol-3-yl]propyl)-4-(H)-piperazine. 3.5 Hydrogen Oxalate 1. 5-(4-tert-Butyloxycarbonyl)piperazin-1-yl pentanal dimethyl acetal a) 5-Bromopentanal dimethyl acetal To a solution of 5-bromovaleryl chloride (50 g, 0.251 mol) in anhydrous THF (500 ml), at −78° C., was added lithium tri-tert-butoxyaluminohydride (1.0M solution in tetrahydrofuran, 300 ml; 0.30 mol), keeping the temperature below −70° C. The solution was stirred at −78° C. for 5 h and then quenched by dropwise addition of 2M hydrochloric acid (350 ml). The mixture was warmed to room temperature and stirred for 16 h. Diethyl ether (500 ml) was added, the aqueous phase separated and extracted further with ether (×2). The combined extracts were washed with saturated $Na_2CO_3$ solution (×1), water (×1) and brine (×2), dried ($Na_2SO_4$) and evaporated to give 5-bromovaleraldehyde (37.5 g, 91%). A solution of 5-bromovaleraldehyde (37.5 g, 0.227 mol) in methanol (250 ml) and concentrated sulphuric acid (0.5 ml) was stirred at room temperature for 3 h. The solvent was removed under vacuum and to the residue was added $K_2CO_3$ solution (50 ml) and diethyl ether (500 ml). The aqueous layer was separated and re-extracted with ether (×2). The combined extracts were washed with water and brine dried ($Na_2SO_4$) and evaporated. The crude product was chromatographed on silica gel eluting with diethyl ether/hexane (1:9) to give the title-acetal (27.5 g, 57%). δ (250MHz, $CDCl_3$) 1.43–1.67 (4H, m, 2 of $CH_2$); 1.83–1.94 (2H, m, $CH_2$); 3.38 (6H. s, CH(OMe)$_2$); 3.42 (2H, t, J=7 Hz, $CH_2Br$), 4.37 (1H, t, J=7 Hz, C$\underline{H}$(OMe)$_2$).

b) 5-(4-tert-Butyloxycarbonyl)piperazin-1-yl pentanal dimethyl acetal

A mixture of 5-bromovaleraldehyde dimethyl acetal (27.5 g. 0.13 mol), $Na_2CO_3$ (20.7 g, 0.195 mol), sodium iodide (19.5 g, 0.13mol) and tert-butyl-1-piperazinecarboxylate (25.5 g, 0.137 mol), in dimethoxyethane (250 ml), was heated at 100° C. for 3 h. Aluminium foil was wrapped around the vessel to exclude light. The mixture was cooled to room temperature and filtered. The filtrate was evaporated under reduced pressure and then EtOAc (50 ml) added and the mixture filtered again to remove inorganic salts. The solvent was removed under vacuum and the residue chromatographed on silica gel eluting with EtOAc to give the title-product (25.7 g, 63%). δ (250MHz, $CDCl_3$) 1.29–1.71 (6H, m, 3 of $CH_2$); 1.46 (9H, s, $OC(Me)_3$); 2.31–2.39 (6H, m, 3 of $CH_2$); 3.32 (6H, s, $CH(OMe)_2$); 3.41–3.45 (4H, m, 2 of $CH_2$); 4.36 (1H, t, J=6Hz, C$\underline{H}$(OMe)$_2$).

2. 1-(3-[5-(1,2,4-Triazol-4-yl)-1H-indol-3-yl]propyl)-4-(H)-piperazine. 3.5 Hydrogen Oxalate A mixture of 4'-(1,2,4-triazol-4-yl)phenylhydrazine (5.0 g, 28.6 mmol) and 5-(4-tert-butyloxycarbonyl)piperazin-1-yl pentanal dimethylacetal (9.03 g, 28.6 mmol) in 4% sulphuric acid (150 ml) was heated at reflux for 48 h. The solution was cooled in an ice-bath, basified with solid $K_2CO_3$ and extracted with butan-1-ol (×3). The solvent was removed under vacuum and azeotroped with hexane (×2). The crude product was purified by chromatography on silica gel eluting with $CH_2Cl_2/MeOH/NH_3$ (30:8:1) to give the title-indole (3.9 g, 44%). The 3.5 hydrogen oxalate salt was prepared using 200 mg of free base: mp 90–92° C. (Found: C, 45.97; H, 4.76; N, 13.77. $C_{17}H_{22}N_6 \cdot 3.5(C_2H_2O_4)$ requires C, 46.08; H, 4.76; N, 13.43%); δ (360MHz, $D_2O$) 2.12–2.24 (2H, m, $CH_2$); 2.93 (2H, t, J=7Hz, $CH_2$); 3.46–3.76 (8H, m, 4 of $CH_2$); 7.37 (1H, dd, J=1.9 and 8.7Hz, Ar-H); 7.39 (1H, s, Ar-H); 7.66 (1H, d, J=8.7, Ar-H); 7.82 (1H, d, J=1.9Hz, Ar-H); 9.13 (2H, s, Triazole-H).

PREPARATION 3

2,2-Difluorophenylacetic acid a) Ethylbenzoyl formate (1.13 g, 0.0063 mol) was dissolved in anhydrous $CH_2Cl_2$ (30 ml) and diethylaminosulfurtrifluoride (DAST, 1.0 ml, 0.0086 mol) added. The reaction mixture was heated to 40° C. and left stirring for 4 h. The reaction was cooled, poured into a mixture of $NaHCO_3$/ice-water and the product extracted into ether (50 ml). The organic layer was dried over ($MgSO_4$), evaporated and the residue chromatographed on silica eluting with 2% ether/petrol to yield 0.96 g (76%) of 2,2-difluorophenylacetic acid ethyl ester as a colourless oil. δ (250MHz, $CDCl_3$) 1.26 (3H, t), 4.29 (2H, q), 7.50 (3H, m), 7.62 (2H, m).

b) The ethyl ester from above was dissolved in $H_2O$/THF (1:1, 20 ml) and cooled to 0° C. Sodium hydroxide (1 g) was added and the reaction stirred for 1 h. TLC (5% ether/hexane) showed complete disappearance of the starting ester. The reaction was acidified to pH 2 with 10% HCl and the product extracted into ether. The organic layer was dried over ($MgSO_4$), filtered and evaporated in vacuo to yield the title compound as a solid (1.0 g).

EXAMPLE 1

1-[3-(5-(1,2,4-Triazol-4-yl)-1H-indol-3-yl)propyl]-4-(2,2-difluoro-2-phenyl)ethanoyl)piperazine hydrochloride 1-[3-(5-(1,2,4-Triazol-4-yl)-1H-indol-3-yl)propyl] piperazine (0.300 g, 0.97 mol) was dissolved in dichloromethane (20 ml) and 2,2-difluorophenylacetic acid (0.400 g, 0.0023 mol) added, followed by triethylamine (0.8 ml, 0.00575 mol). The reaction was stirred for 2 h at 25° C., diluted with ethyl acetate (60 ml) and washed with water (30 ml) and brine. The organic layer was dried over $MgSO_4$, and removed in vacuo. The residue was chromatographed on silica eluting with 1–3% MeOH—$CH_2Cl_2$ to obtain 0.125 g of the title compound. 0.030 g of the free base was converted to the HCl salt by treating with HCl/MeOH to yield a white solid. MS (m/e) 465 (100%, M+1) $^1$H NMR (free base, 250MHz, $CDCl_3$) δ 1.68 (1H, m), 1.88 (2H, m), 2.17 (1H, br m), 2.26 (4H, m), 2.77 (2H, t, J=3Hz), 3.47 (2H, m), 3.72 (2H, m).

EXAMPLE 2

A mixture of 1-[3-(5-(1,2,4-Triazol-4-yl)-1H-indol-3-yl) propyl]piperazine (20 mg, 64.5 μmol), a carboxylic acid (130 μmol), 1-(3-dimethylaminopropyl)-3-ethylcarbodiimide methiodide (38 mg, 130 μmol) and hydrobenzotriazole (1 mg) were dissolved in DMF (300 μl) and stood at room temperature for 18 h.

Meanwhile Amberlyst 15 ion exchange resin (1 g) was washed with 1N HCl, 1N NaOH, 3% $NH_3$ in MeOH, 1N HCl, then MeOH. The reaction mixture was diluted with MeOH (1 ml) and applied to the resin, which was then washed with MeOH (3 ml), $H_2O$ (2 ml) and MeOH (3 ml). The product was then eluted with 3% $NH_3$ in MeOH (2 ml) and evaporated. Products were >80% pure by HPLC.

The following compounds were made in this way using 1-phenyl-1-cyclopentylmethanoic acid, 2-phenoxybenzoic acid, (R,S)-2-(2-fluorophenyl)propanoic acid, (R,S)-2-(3-fluorophenyl)-propanoic acid, (R,S)-2-(4-fluorophenyl) propanoic acid and 4-fluorophenylethanoic acid respectively, all of which acids are available commercially.

1-[3-(5-(1,2,4-Triazol-4-yl)-1H-indol-3-yl)propyl]-4-(1-phenyl-1-cyclopentylmethanoyl)piperazine: MS (m/e) 483 (M+1).

1-[3-(5-(1,2,4-Triazol-4-yl)-1H-indol-3-yl)propyl]-4-(2-phenoxybenzoyl)piperazine: MS (m/e) 507 (M+1).

1-[3-(5-(1,2,4-Triazol-4-yl)-1H-indol-3-yl)propyl]-4-[(R,S)-2-(2-fluorophenyl)propanoyl]piperazine: MS (m/e) 461 (M+1).

1-[3-(5-(1,2,4-Triazol 4-yl)-1H-indol-3-yl)propyl]-4-[(R,S)-2-(3-fluorophenyl)propionanoyl]piperazine: MS (m/e) 461 (M+1).

1-[3-(5-(1,2,4-Triazol-4-yl)-1H-indol-3-yl)propyl]-4-[(R,S)-2-(4-fluorophenyl)propanoyl]piperazine: MS (m/e) 461 (M+1).

1-[3-(5-(1,2,4-Triazol-4-yl)-1H-indol-3-yl)propyl]-4-(4-fluorophenylethanoyl)piperazine: MS (m/e) 447 (M+1).

We claim:

1. A compound of Formula I, or a salt thereof:

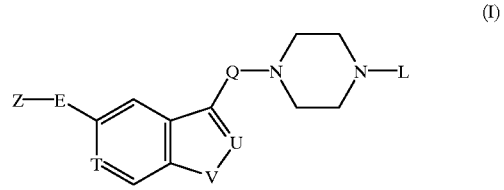

(I)

wherein

Z represents a 1,2,4-triazole ring which is optionally substituted with methyl, ethyl, benzyl, or amino;

E represents a chemical bond or a methylene linkage;

Q represents a propylene chain;
T represents CH;
U represents C—$R^2$;
V represents $NR^3$;
$R^2$ and $R^3$ independently represent hydrogen or $C_{1-6}$ alkyl; and
L is selected from the group consisting of:

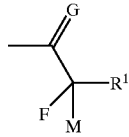

(A)

wherein G represents oxygen;
M represents fluoro or methyl; and
$R^1$ is selected from the group consisting of phenyl, fluorophenyl and difluorophenyl.

2. A compound which is:
4-(2,2-difluoro-1-oxo-2-phenylethyl)-1-[3-(5-(1,2,4-triazol-4-yl)-1H-indol-3-yl)propyl]piperazine or a salt thereof.

3. A compound which is:
1-[3-(5-(1,2,4-triazol-4-yl)-1H-indol-3-yl)propyl]-4-(1-phenyl-1-cyclopentylmethanoyl)piperazine;
1-[3-(5-(1,2,4-triazol-4-yl)-1H-indol-3-yl)propyl]-4-(2-phenoxybenzoyl)piperazine;
1-[3-(5-(1,2,4-triazol-4-yl)-1H-indol-3-yl)propyl]-4-[(R,S)-2-(2-fluorophenyl)propanoyl]piperazine;
1-[3-(5-(1,2,4-triazol-4-yl)-1H-indol-3-yl)propyl]-4-[(R,S)-2-(3-fluorophenyl)propanoyl]piperazine;
1-[3-(5-(1,2,4-triazol-4-yl)-1H-indol-3-yl)propyl]-4-[(R,S)-2-(4-fluorophenyl)propanoyl]piperazine;
1-[3-(5-(1,2,4-triazol-4-yl)-1H-indol-3-yl)propyl]-4-(4-fluorophenylethanoyl)piperazine;
or a salt thereof.

4. A process for preparing a compound of formula I as defined in claim 1 which process comprises:

(A) when G in the compound of formula I represents oxygen, reacting a compound of formula III with a compound of formula IV:

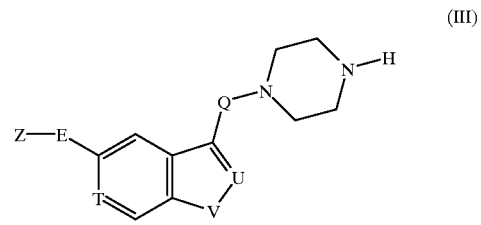

(III)

wherein Z, E, Q, T, U, V and L are as defined in claim 1.

5. A pharmaceutical composition comprising a compound as defined in claim 1, or a pharmaceutically acceptable salt thereof, and a pharmaceutically acceptable carrier.

6. A method of treatment of a subject suffering from or prone to migraine, cluster headache, chronic paroxysmal hemicrania, headache associated with vascular disorders, tension headache, and paediatric migraine, which comprises administering to that subject a therapeutically effective amount of a compound according to claim 1 or a pharmaceutically acceptable salt thereof.

* * * * *